(12) United States Patent
Takizawa et al.

(10) Patent No.: US 8,918,167 B2
(45) Date of Patent: Dec. 23, 2014

(54) RI MEASUREMENT/NOTIFICATION APPARATUS AND MEASUREMENT/NOTIFICATION PROGRAM

(71) Applicant: Nihon Kohden Corporation, Shinjuku-ku, Tokyo (JP)

(72) Inventors: Koji Takizawa, Tokyo (JP); Tatsuo Nishihara, Tokyo (JP); Yuuho Iwanaga, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 14 days.

(21) Appl. No.: 13/764,113

(22) Filed: Feb. 11, 2013

(65) Prior Publication Data
US 2013/0245475 A1 Sep. 19, 2013

(30) Foreign Application Priority Data
Mar. 15, 2012 (JP) .................................. 2012-058741

(51) Int. Cl.
*A61B 5/046* (2006.01)
*A61B 5/044* (2006.01)
*A61B 5/04* (2006.01)

(52) U.S. Cl.
CPC ............. *A61B 5/044* (2013.01); *A61B 5/04012* (2013.01); *A61B 5/046* (2013.01)
USPC ....................................................... 600/518

(58) Field of Classification Search
USPC ........................................................ 600/518
See application file for complete search history.

(56) References Cited

U.S. PATENT DOCUMENTS

| 7,117,030 | B2* | 10/2006 | Berenfeld et al. ............ 600/515 |
| 2008/0161658 | A1* | 7/2008 | Tashiro et al. ................ 600/301 |
| 2009/0112109 | A1* | 4/2009 | Kuklik et al. ................. 600/515 |
| 2009/0112110 | A1 | 4/2009 | Zhang |
| 2009/0204113 | A1* | 8/2009 | MacAdam et al. ............. 606/41 |
| 2010/0094274 | A1 | 4/2010 | Narayan et al. |
| 2010/0137861 | A1 | 6/2010 | Soroff et al. |

OTHER PUBLICATIONS

Search Report dated Jun. 26, 2013 issued by the European Patent Office in counterpart European Patent Application No. 13158273.6.
Jerome Kalifa, et al; "Mechanisms of Wave Fractionation at Boundaries of High-Frequency Excitation in the Posterior Left Atrium of the Isolated Sheep Heart During Atrial Fibrillation", Circulation Journal of the American Heart Association, Feb. 7, 2006, vol. 113, pp. 626-633 (9 sheets).

* cited by examiner

*Primary Examiner* — Michael Kahelin
(74) *Attorney, Agent, or Firm* — Sughrue Mion, PLLC

(57) ABSTRACT

An RI measurement/notification apparatus includes: a displaying section configured to display waveform data of an intracardiac electrocardiogram; a waveform data acquiring section configured to acquire waveform data in a preset waveform data acquisition time period from an intracardiac electrocardiogram during atrial fibrillation; an RI calculating section configured to calculate an RI value based on the waveform data acquired by the waveform data acquiring section; and a notifying section configured to, in a case where the RI value calculated by the RI calculating section exceeds a preset threshold, notify that the value exceeds the threshold.

6 Claims, 4 Drawing Sheets

RI MEASUREMENT/NOTIFICATION APPARATUS AND MEASUREMENT/NOTIFICATION PROGRAM

BACKGROUND OF THE INVENTION

The present invention relates to an RI measurement/notification apparatus and measurement/notification program for notifying that an abnormality occurs in an RI value (an index value for determining an existence of a rotor).

Atrial fibrillation is a frequent tachyarrhythmia. Researches on finding a mechanism for maintaining atrial fibrillation, and a method of treating it have been conducted. Examples of the treatment method are drug treatment (symptomatic treatment), catheter ablation (radical treatment). Among the methods, catheter ablation is treatment in which the behavior of a heart during atrial fibrillation is analyzed based on an intracardiac electrocardiogram, a portion where an electric signal (excitation wave) called a rotor is generated is identified, and the portion is removed away to suppress the generation of a rotor.

As a method of analyzing an intracardiac electrocardiogram of a heart during atrial fibrillation, for example, an analysis method has been proposed in which the RI (Regularity Index) is calculated to find a rotor (see Non-patent Document 1).

(Non-patent Document 1) Circulation Feb. 7, 2006 Fractionation at the Posterior Left Atrium, Kalifa et al.

According to the analysis method disclosed in Non-patent Document 1, an evaluating person can identify the position of a rotor by evaluating the value of a calculated RI. Conventionally, however, there is no measurement apparatus which detects in real time an RI from an intracardiac electrocardiogram of a heart during atrial fibrillation, and which notifies that an abnormality occurs in the RI value. Also Non-patent Document 1 does not disclose such an apparatus. In the case where a plurality of RI values are to be automatically detected, therefore, an evaluating person cannot rapidly determine which one of electrodes of a cardiac catheter measures an abnormal value.

SUMMARY

Therefore, the invention has been conducted in view of the problem. It is an aspect of the invention to provide an RI measurement/notification apparatus and measurement/notification program which can calculate an RI from an intracardiac electrocardiogram and notify the existence of a rotor.

It is therefore an aspect of the invention to provide an RI measurement/notification apparatus including:

a displaying section configured to display waveform data of an intracardiac electrocardiogram;

a waveform data acquiring section configured to acquire waveform data in a preset waveform data acquisition time period from an intracardiac electrocardiogram during atrial fibrillation;

an RI calculating section configured to calculate an RI value based on the waveform data acquired by the waveform data acquiring section; and a notifying section configured to, in a case where the RI value calculated by the RI calculating section exceeds a preset threshold, notify that the value exceeds the threshold.

The notifying section may perform the notification by displaying information that the value exceeds the threshold, on the displaying section.

The notifying section may notify that the value exceeds the threshold, associating with waveform data displayed on the displaying section.

The notifying section may perform the notification while, in the waveform data displayed on the displaying section, a portion of waveform data corresponding to a place where the RI value is abnormal is shown in a different color.

The notifying section may perform the notification while, in the waveform data displayed on the displaying section, a portion of waveform data corresponding to a place where the RI value is abnormal is shown in a boxed area.

It is another aspect of the invention to provide a measurement/notification program which causes a computer to execute following procedures:

a waveform data acquisition procedure of acquiring waveform data in a preset waveform data acquisition time period from waveform data of an intracardiac electrocardiogram during atrial fibrillation, the intracardiac electrocardiogram being displayed on a displaying section;

an RI calculation procedure of calculating an RI value based on the waveform data acquired in the waveform data acquisition procedure; and a notification procedure of, in a case where the RI value calculated in the RI calculation procedure exceeds a preset threshold, notifying that the value exceeds the threshold.

In the notification procedure, the notification may be performed by showing information indicating that the value exceeds the threshold, in a pop-up window.

BRIEF DESCRIPTION OF THE DRAWINGS

FIG. 3A is a view showing an intracardiac electrocardiogram waveform which was measured in the atrium, FIG. 3B is a view showing a waveform which is obtained by full-wave rectifying the intracardiac electrocardiogram waveform, and FIG. 3C is a view showing a waveform which is obtained by performing an FFT on the intracardiac electrocardiogram waveform, and the calculated RI value.

DETAILED DESCRIPTION OF EMBODIMENTS

Hereinafter, an embodiment of an RI measurement/notification apparatus of the invention will be described with reference to the accompanying drawings.

Figure 1:
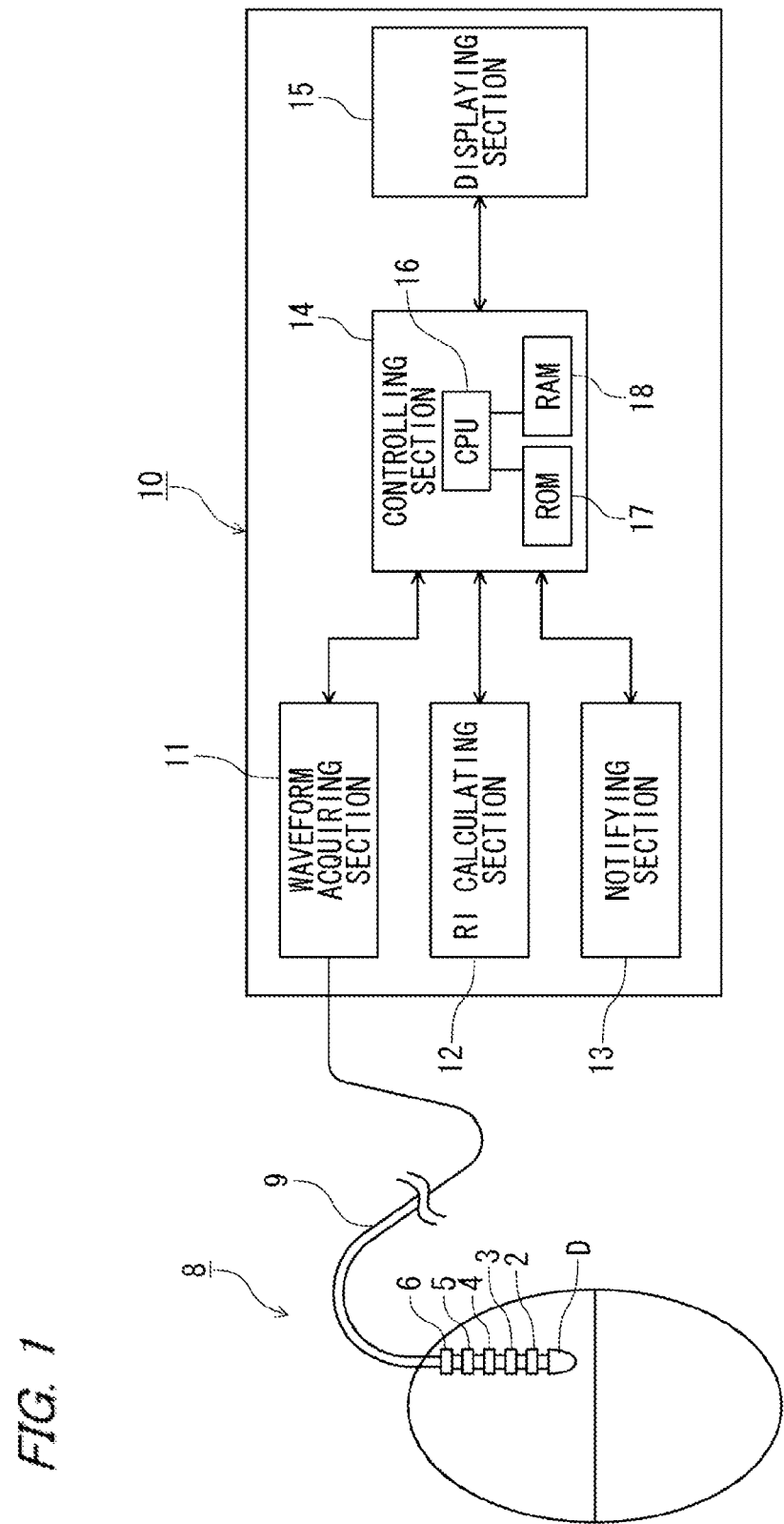
FIG. 1 is a block diagram showing the configuration of the RI measurement/notification apparatus of the invention.

An RI measurement/notification apparatus 10 shown FIG. 1 includes: a waveform acquiring section 11 (an example of the waveform data acquiring section) for acquiring data of an intracardiac electrocardiogram waveform which comply with predetermined conditions, from measured intracardiac electrocardiogram waveforms; an RI calculating section 12 for calculating an RI (Regularity Index) value from an intracardiac electrocardiogram waveform; a notifying section 13 for, in the case where the RI value satisfies the predetermined conditions, notifying that the condition is satisfied; a displaying section 15 for displaying waveform data of an intracardiac electrocardiogram, and data indicating that the RI value satisfies predetermined conditions; and a controlling section 14 for controlling these sections. The RI value means an index value for determining an existence of a rotor (the value will be described later in detail).

The reference numeral 8 in FIG. 1 diagrammatically indicates the heart in which an intracardiac electrocardiogram in the atrium is measured. A cardiac catheter 9 is inserted from a peripheral vessel into the atrium to acquire an intracardiac electrocardiogram waveforms. Portions D, 2, 3, 4, 5, 6 which are disposed in the cardiac catheter 9 are electrodes for measuring intracardiac electrocardiogram waveforms. An intracardiac electrocardiogram waveform can be obtained in each of multi channels such as the electrodes D-2, the electrodes 3-4, and the electrodes 5-6. The number of electrodes is not limited to that in the embodiment, and a larger number of electrodes may be disposed. Data of an acquired intracardiac electrocardiogram waveforms are sent to the RI measurement/notification apparatus 10 through the cardiac catheter 9, and then acquired by the waveform acquiring section 11 of the RI measurement/notification apparatus 10.

The waveform acquiring section 11 acquires data of the intracardiac electrocardiogram waveforms based on a waveform data acquisition control signal transmitted from the controlling section 14. The waveform data acquisition control signal contains control signals indicative of a timing and period of time for acquiring intracardiac electrocardiogram waveform data. The waveform data acquisition time period in the invention is an example of the time period for acquiring waveform data of the intracardiac electrocardiogram. A preset waveform data acquisition time period is transmitted as an acquisition time period control signal from the controlling section 14 to the waveform acquiring section 11. The waveform acquiring section 11 which receives the acquisition time period control signal acquires intracardiac electrocardiogram waveform data in the time period for acquiring waveform data starting from the received acquisition timing. The acquired intracardiac electrocardiogram waveform data are transmitted to the controlling section 14, and then stored in a RAM 18 and flash memory (not shown) mounted in the controlling section 14.

The RI calculating section 12 calculates the RI value from the data of the intracardiac electrocardiogram waveforms, based on an RI calculation control signal transmitted from the controlling section 14. The RI value is a ratio of the amplitude at the DF (Dominant Frequency) to the total sum of amplitudes at frequencies constituting an intracardiac electrocardiogram. The amplitude at the DF is the amplitude at a frequency where the largest amplitude is obtained when a frequency analysis is performed by an FFT (Fast Fourier Transform). The intracardiac electrocardiogram waveform data (intracardiac electrocardiogram waveform data which are acquired by the waveform acquiring section 11 during the waveform data acquisition time period) stored in the RAM 18 are transmitted from the controlling section 14 to the RI calculating section 12. The RI calculating section 12 calculates the RI value based on the intracardiac electrocardiogram waveform data. The procedure of calculating the RI will be described later with reference to FIGS. 2 to 4. The data of the calculated RI value are transmitted to the controlling section 14, and then stored in the RAM 18 and flash memory (not shown) mounted in the controlling section 14.

If it is determined that the calculated RI value satisfies predetermined conditions, based on a notification control signal transmitted from the controlling section 14, the notifying section 13 notifies it. The RI value (the RI data which have been calculated by the RI calculating section 12, and stored in the RAM 18) is transmitted from the controlling section 14 to the notifying section 13. The notifying section 13 compares the received RI value with a predetermined threshold, and, if it is determined that the RI value exceeds the threshold, transmits data indicating that the RI value exceeds the threshold, to the controlling section 14 to notify it.

For example, the notified data includes the following data: data of the calculated RI value; data of a graph which is obtained by performing an FFT on the acquired intracardiac electrocardiogram waveform data; data of the DF value which is detected by the FFT; data indicating that these data are to be displayed in a pop-up window or switching a display screen on the displaying section 15 (that is, the acquired intracardiac electrocardiogram waveforms are displayed on the displaying section); and data indicating that data are displayed while intracardiac electrocardiogram waveform data and data in the pop-up window are correlated with each other. Specifically, the data includes: those indicating that, among the intracardiac electrocardiogram waveform data displayed on the displaying section 15, waveform data of a portion corresponding to a place of an abnormality of the RI value (the value exceeds the predetermined threshold) are displayed while changing the color of the portion; and those indicating that, among the intracardiac electrocardiogram waveform data, waveform data of the portion corresponding to the place of the abnormality of the RI value are shown in a boxed area or a hatched area; data indicating that a predetermined place (an icon or the like) of the displaying section 15, or a lamp or indicator disposed in other than the displaying section 15 is lighted or blinked, or the color tone of the portion is changed. In addition, an item which, when displayed on the displaying section 15, causes the existence of a rotor to be visually recognized easily and rapidly from the displayed data may be preferably displayed as data notifying that the value exceeds the threshold. The data transmitted to the controlling section 14 (data indicating that the RI value exceeds the threshold) are stored in the RAM 18 and flash memory (not shown) mounted in the controlling section 14.

Based on a display control signal transmitted from the controlling section 14, the displaying section 15 displays data stored in the RAM 18, such as the intracardiac electrocardiogram waveform data which are measured by the electrodes of the cardiac catheter 9, the intracardiac electrocardiogram waveform data during the waveform data acquisition time period obtained by the waveform acquiring section 11, and the data indicating that the RI value exceeds the threshold, on the display screen. These data can be read out from the memory to be displayed on the displaying section 15 during the measurement of an intracardiac electrocardiogram waveform, i.e., in real time, and also in the case where, after the measurement, data of the intracardiac electrocardiogram waveform are to be subjected to review, or the like.

The controlling section 14 controls the various portions (the waveform acquiring section 11, the RI calculating section 12, the notifying section 13, and the displaying section 15) of the RI measurement/notification apparatus 10. The controlling section 14 includes: a CPU 16 which governs the control; a ROM 17 which retains programs for executing various process procedures in the CPU; and the RAM 18 which stores various data acquired or calculated by, or notified to the various portion (the acquiring section, the calculating section, the notifying section, etc.), as a work area for the CPU. The controlling section further includes the flash memory which is not shown. Various data acquired or calculated by, or notified to the various portion (the acquiring section, the calculating section, the notifying section, etc.) are stored also in the flash memory. Both in the case where the intracardiac electrocardiogram waveform data are analyzed in real time, and the case where the intracardiac electrocardiogram waveform data are analyzed in a review analysis, a discussion, or the like, the controlling section 14 can cause the various data stored in the memories to be displayed on the displaying section 15, to notify that there is an abnormality of the RI value, namely a rotor exists in the atrium.

Figure 2:
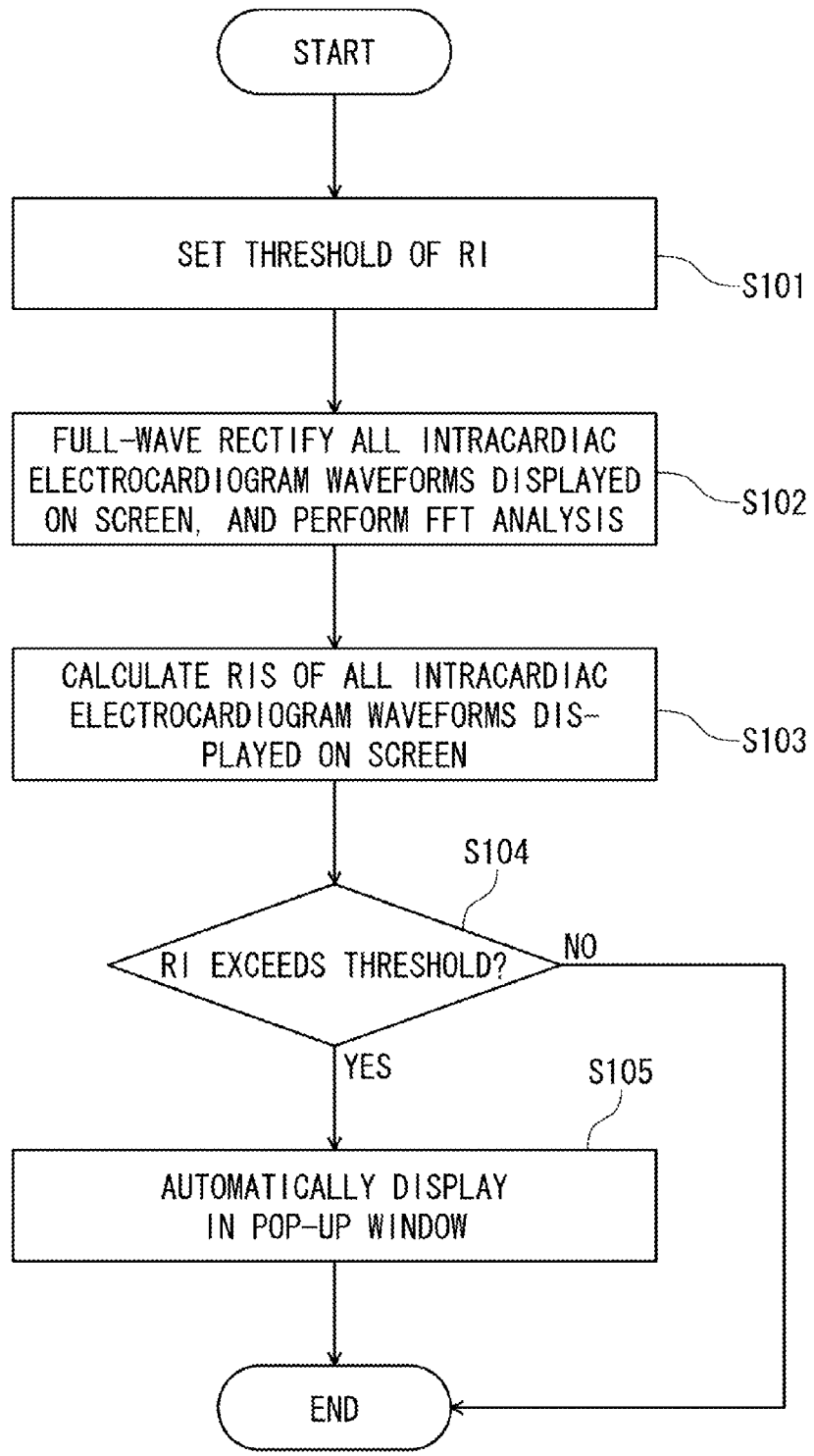
FIG. 2 is a flowchart showing a process procedure of a RI measurement and notification process.
Figure 3A:
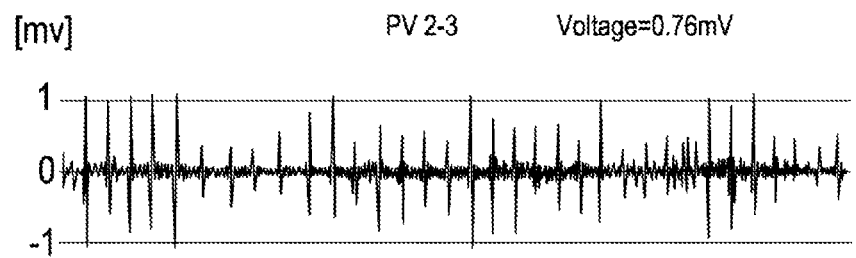
FIGS. 3A to 3C are views showing a process of calculating an RI value.
Figure 3B:
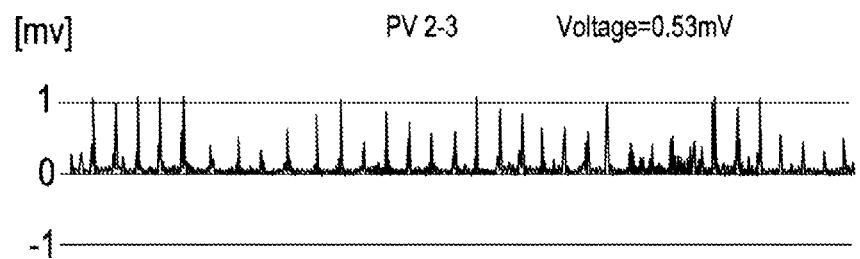
Figure 3C:
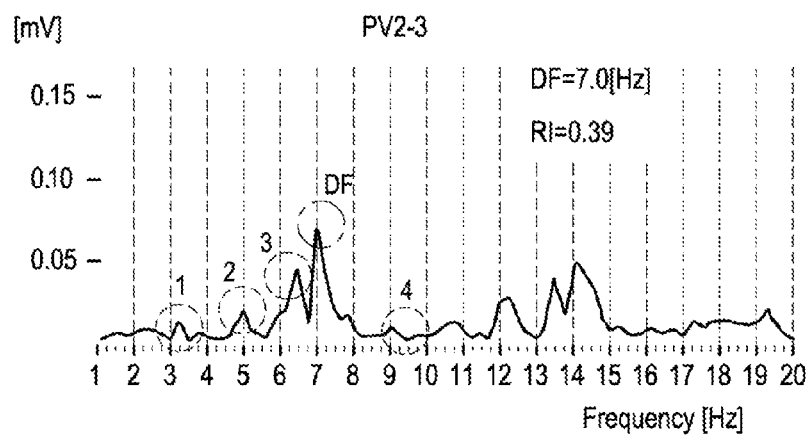
Figure 4:
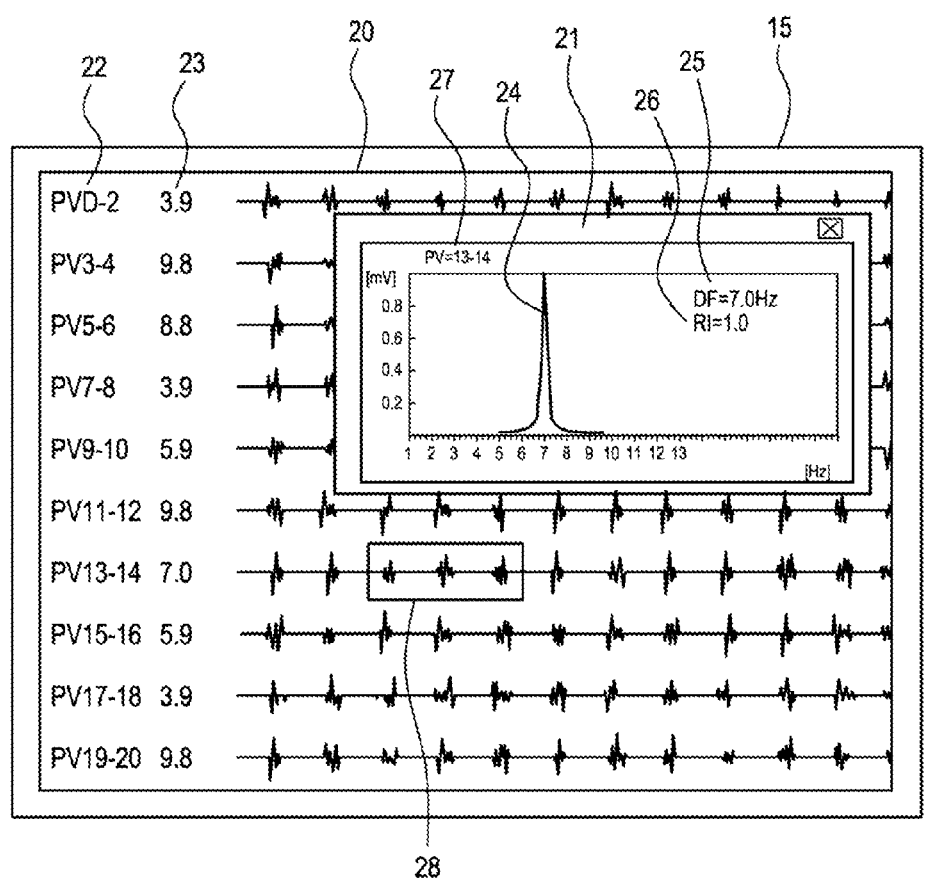
FIG. 4 is a view of a displaying section on which an intracardiac electrocardiogram is displayed, and an FFT graph and the RI value are displayed in a pop-up window.

Next, the process procedure of the RI measurement and notification process will be described with reference to the flowchart shown in FIG. 2. The process procedure will be described also with reference to FIGS. 3A to 3C showing the procedure of calculating the RI value, and FIG. 4 showing data in a pop-up window on the displaying section 15.

When the process of measuring and notifying the RI (Regularity Index) value is started, a process of setting a threshold for the RI which is an index value for determining the existence of a rotor is first performed (step S101). The threshold can be set or changed from the outside. For example, the threshold may be input or changed by setting/inputting means (not shown) which is connected to the RI measurement/notification apparatus 10. The RI value is indicated by a numerical value which is not greater than 1. In the embodiment, specifically, the threshold for the RI is set to 0.7.

Next, the waveform acquiring section 11 acquires waveform data during the waveform data acquisition time period from the intracardiac electrocardiogram waveform data measured by the cardiac catheter 9. The acquired intracardiac electrocardiogram waveform data are stored in the RAM 18 and flash memory (not shown) of the controlling section 14, and caused by the controlling section 14 to be displayed on the displaying section 15.

Then, the RI calculating section 12 full-wave rectifies all intracardiac electrocardiogram waveforms displayed on the displaying section 15, and performs a fast Fourier transform (FFT) process on the full-wave rectified waveforms (step S102). Specifically, first, the intracardiac electrocardiogram waveform data acquired by the waveform acquiring section 11 are transmitted from the controlling section 14 to the RI calculating section 12. The RI calculating section 12 full-wave rectifies the received intracardiac electrocardiogram waveform data. FIG. 3A shows one waveform data of the intracardiac electrocardiogram waveform data displayed on the displaying section 15, and FIG. 3B shows waveform data which are obtained by full-wave rectifying the intracardiac electrocardiogram waveform data of FIG. 3A. The intracardiac electrocardiogram waveform data are measured by the cardiac catheter 9 including the plurality of electrodes. A plurality of intracardiac electrocardiogram waveform data measured by the plurality of electrodes are displayed on the displaying section 15. FIG. 3A shows the intracardiac electrocardiogram waveform data measured by the electrodes 2-3 among the electrodes.

Next, the RI calculating section 12 performs an FFT process on the full-wave rectified waveform data (FIG. 3B). FIG. 3C shows data which are obtained by performing an FFT process on the full-wave rectified waveform of FIG. 3B. In FIG. 3C, a graph of the waveform which has undergone the FFT process, the DF value, and the RI value are shown. The DF means the frequency where the largest amplitude is obtained when a frequency analysis is performed by the FFT process, and indicated the most superior periodic excitation. In FIG. 3C, DF=7.0 [Hz], and the frequency (indicated by a hollow circle) of the OF which is the frequency where the largest amplitude is obtained in the waveform shown in the graph is indicated. In a manner similar to that of the above-described specific process, full-wave rectification and an FFT process are performed on all intracardiac electrocardiogram waveform data which are measured by the plurality of electrodes.

Then, the RI calculating section 12 performs an RI calculation process on all intracardiac electrocardiogram waveforms which are displayed in the screen of the displaying section 15 (step S103). The RI is obtained by calculating a ratio of the amplitude at the DF to the total sum of amplitudes at frequencies constituting an intracardiac electrocardiogram. As described above, FIG. 3C shows data which are obtained by performing full-wave rectification and an FFT process on the intracardiac electrocardiogram waveform data measured by the electrodes 2-3 among the plural electrodes. The RI value shown in FIG. 3C is calculated by a calculation expression of RI=amplitude of DF/(amplitude of 1+amplitude of 2+amplitude of 3+amplitude of DF+amplitude of 4) where "amplitude of 1" indicates the maximum amplitude in the region of hollow circle 1 in FIG. 3C, "amplitude of 2" indicates the maximum amplitude in the region of hollow circle 2, "amplitude of 3" indicates the maximum amplitude in the region of hollow circle 3, "amplitude of DF" indicates the maximum amplitude in the region of hollow circle DF, and "amplitude of 4" indicates the maximum amplitude in the region of hollow circle 4. In the case of FIG. 3C, the value calculated by the expression is RI=0.39. In a similar manner as the above-described process, a process of calculating the RI is performed on all intracardiac electrocardiogram waveform data which are measured by the plurality of electrodes. The full-wave rectified data, FFT data, and RI data (data between electrodes corresponding to FIGS. 3B and 3C) related to calculated intracardiac electrocardiograms between the electrodes are stored in the RAM 18 and flash memory (not shown) mounted in the controlling section 14. These data may be displayed on the displaying section 15 in response to an operation which is conducted on displaying means (not shown) connected to the RI measurement/notification apparatus 10.

Then, the RI calculating section 12 determines whether the calculated RI values exceed the threshold or not (step S104). If it is determined that all the RI values do not exceed the threshold (step S104: No), the RI measurement and notification process is ended. In the case shown in FIG. 3C, the threshold for the RI is set to 0.7 as described above, and therefore the RI value (0.39) which is calculated here does not exceed the threshold (0.7). Consequently, it is possible to determine that a rotor does not exist in the intracardiac electrocardiogram waveform (FIG. 3A) measured by the electrodes 2-3, and the RI measurement and notification process is ended.

By contrast, if it is determined that any one of the RI values exceeds the threshold (step S104: Yes), data indicating that the RI value exceeds the threshold are displayed in a pop-up window (step S105). FIG. 4 shows a manner in which data indicating that the threshold is exceeded are displayed on the displaying section 15. A screen 21 notifying that the RI value exceeds the threshold is displayed in a pop-up window in a partial region of a screen 20 displaying the intracardiac electrocardiogram waveforms measured by the electrodes.

The identifications of the combinations of electrodes which measure the intracardiac electrocardiogram waveforms are displayed in a region 22 of the screen 20. For example, "PVD-2" indicates that the corresponding intracardiac electrocardiogram waveform was measured by the electrodes D, 2 of the cardiac catheter 9. It is seen that, in the embodiment, the intracardiac electrocardiogram waveforms were measured by using a cardiac catheter having 20 electrodes. In a region 23, DF values [Hz] calculated based on the intracardiac electrocardiogram waveforms are displayed.

In the screen 21, a graph 24 which is obtained by performing full-wave rectification and an FFT process on the intracardiac electrocardiogram waveform, the DF value 25, the RI value 26, the identification 27 of the electrode combination are displayed. The screen 21 shows that the DF value is 7.0 Hz, the RI value is 1.0, and the intracardiac electrocardiogram was measured by electrodes 13, 14. Since the threshold for the RI is set to 0.7 as described above, "RI=1.0" notifies that the RI exceeds the threshold. Moreover, "PV13-14" shown in the electrode combination identification 27 is displayed associated with the electrode combination identification (PV13-14) shown in the region 22 of the screen 20. Furthermore, "DF=7.0 Hz" is displayed associated with the DF value (7.0) shown in the region 23 of the screen 20.

As displayed in the screen 21, the RI value calculated from the intracardiac electrocardiogram waveform of PV13-14 exceeds the threshold and exhibits an abnormal value. The portion of the intracardiac electrocardiogram waveform of PV13-14 in the screen 20 corresponding to the place of the abnormality of the RI value may be displayed in a box 28, whereby information indicating that the RI exceeds the threshold may be displayed associated with the intracardiac electrocardiogram waveform. In another manner of displaying association, the portion of the intracardiac electrocardiogram waveform corresponding to the place of the abnormality of the RI value may be displayed in a color which is different from the display color of the portion of the intracardiac electrocardiogram waveform not corresponding to the abnormal place.

In the case where, in addition to the intracardiac electrocardiogram waveform of PV13-14, there is another intracardiac electrocardiogram waveform having an RI value exceeding the threshold, in the intracardiac electrocardiogram waveforms displayed in the screen 20, information that such a waveform exists is displayed, and data indicating that the RI value exceeds the threshold are displayed in another screen other than the screen 21. In this case, the screen 21 and the other screen may be alternately switchingly displayed in a pop-up window on the displaying section 15, by an operation on switching means (not shown) connected to the RI measurement/notification apparatus 10.

The RI measurement/notification apparatus of the embodiment of the invention is configured as described above, and therefore can rapidly detect in which one of waveforms between the electrodes an abnormality exists, and immediately notify the existence. Consequently, an existence of a rotor can be rapidly known, the position of the rotor can be correctly identified, and the portion where the rotor is generated can be promptly eliminated.

In the case where the measured RI value shows an abnormal value which exceeds the threshold, an FFT graph and the RI value indicating the abnormal value are displayed in a pop-up window on the displaying section 15. Therefore, it is possible to rapidly know generation of a rotor in real time while measuring an intracardiac electrocardiogram.

Moreover, the data shown in the pop-up window are displayed associated with waveform data of intracardiac electrocardiograms corresponding to electrodes of the cardiac catheter. Therefore, the existence of a rotor and the position of the rotor (the positions of electrodes which measure the intracardiac electrocardiogram in question) can be known rapidly and correctly.

When an intracardiac electrocardiogram waveform corresponding to the place of an abnormality of the RI value is displayed in a color which is different from the color of the other waveform (of a normal place), or when the portion of an intracardiac electrocardiogram waveform corresponding to the place of the abnormality is shown in, for example, a boxed area or a hatched area, the existence of a rotor and the position of the rotor can be visually known easily and rapidly.

These functions of the RI measurement/notification apparatus are effective in the case where data of intracardiac electrocardiograms during atrial fibrillation are analyzed in real time, and also in the case where data of intracardiac electrocardiograms are analyzed by review analysis, discussion analysis, or the like.

The process procedures which have been described in the embodiment of the invention may be configured as an invention of a method including a series of procedures, or as an invention of a program which causes a computer to execute the series of procedures. Also in this case, effects which are similar to those of the embodiment can be attained.

An RI value can be rapidly calculated form the measured intracardiac electrocardiogram, and, based on the calculated RI value, the existence of a rotor in the atrium is promptly detected and notified.

The invention can be used, for example, in the field of treatment of atrial fibrillation by using cardiac catheterization.

What is claimed is:

1. A regularity index measurement/notification apparatus including:
    a displaying section configured to display waveform data of an intracardiac electrocardiogram;
    a waveform data acquiring section configured to acquire waveform data in a preset waveform data acquisition time period from an intracardiac electrocardiogram during atrial fibrillation;
    a regularity index calculating section configured to calculate a regularity index value based on the waveform data acquired by the waveform data acquiring section; and
    a notifying section configured to, in a case where the regularity index value calculated by the regularity index calculating section exceeds a preset threshold, notify that the value exceeds the threshold,
    wherein the notifying section is configured to notify that the value exceeds the threshold, in such a way that the value and a portion of the waveform data where the regularity index value exceeds the threshold are displayed on the displaying section to be correlated with each other, and
    wherein the display section, the waveform data acquiring section, the regularity index calculating section, and the notifying section perform functions thereof in real time.

2. The regularity index measurement/notification apparatus according to claim 1, wherein the notifying section is configured to perform the notification by displaying information that the value exceeds the threshold, on the displaying section.

3. The regularity index measurement/notification apparatus according to claim 1, wherein the notifying section is configured to perform the notification while, in the waveform data displayed on the displaying section, a portion of waveform data corresponding to a place where the regularity index value is abnormal is shown in a different color from other portion of the waveform data.

4. The regularity index measurement/notification apparatus according to claim 1, wherein the notifying section is configured to perform the notification while, in the waveform data displayed on the displaying section, a portion of waveform data corresponding to a place where the regularity index value is abnormal is shown in a boxed area.

5. A non-transitory computer-readable recording medium having embodied thereon a program which when executed causes a computer to execute a method of notifying a user that an abnormality occurs in a regularity index value, the method comprising:
- acquiring waveform data in a preset waveform data acquisition time period from waveform data of an intracardiac electrocardiogram during atrial fibrillation, the intracardiac electrocardiogram being displayed on a displaying section;
- calculating a regularity index value based on the waveform data acquired in the waveform data acquisition procedure; and
- in a case where the regularity index value exceeds a preset threshold, notifying that the value exceeds the threshold, in such a way that the value and a portion of the waveform data where the regularity index value exceeds the threshold are displayed to be correlated with each other, and
- wherein the display section, the waveform data acquiring section, the regularity index calculating section, and the notifying section perform functions thereof in real time.

6. The non-transitory computer-readable recording medium according to claim 5, wherein the notifying comprises showing information indicating that the value exceeds the threshold, in a pop-up window.

* * * * *